United States Patent [19]

Demassey et al.

[11] Patent Number: 4,925,862

[45] Date of Patent: May 15, 1990

[54] NOVEL PYRETHRINOIDS

[75] Inventors: Jacques Demassey, Montevrain; Jean-Pierre Demoute, Montreuil-Sous-Bois; Jean Tessier, Vincennes, all of France

[73] Assignee: Roussel Uclaf, Paris, France

[21] Appl. No.: 221,948

[22] Filed: Jul. 20, 1988

[30] Foreign Application Priority Data

Jul. 20, 1987 [FR] France .................. 87 10202

[51] Int. Cl.$^5$ .................. C07D 277/34; A01N 43/78; A01N 53/00
[52] U.S. Cl. .................. 514/369; 548/187; 548/146; 548/232; 548/239
[58] Field of Search .................. 548/187; 514/369

[56] References Cited

U.S. PATENT DOCUMENTS 4,083,989  4/1978  Kohn .................. 548/187

FOREIGN PATENT DOCUMENTS 123719  11/1984  European Pat. Off. ............ 548/232
275742   7/1988  European Pat. Off. ............ 548/232
42-1283  1/1967  Japan .................. 548/187

*Primary Examiner*—Robert Gerstl
*Attorney, Agent, or Firm*—Bierman and Muserlian

[57] ABSTRACT

All stereoisomeric forms and mixtures thereof of a compound of the formula

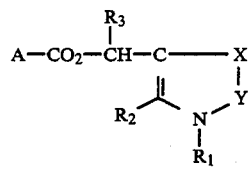

wherein X is —O— or —S—, Y is —C≡O,

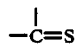

or —CH$_2$—, R$_1$ is selected from the group consisting of hydrogen, halogen, optionally unsaturated alkyl of 1 to 8 carbon atoms and optionally unsaturated cycloalkyl of 3 to 8 carbon atoms, the latter two being optionally substituted with one or more halogen and aryl of 6 to 14 carbon atoms, R$_2$ is selected from the group consisting of hydrogen, —CF$_3$, —NO$_2$, —CN, halogen, alkoxy of 1 to 8 carbon atoms, aryl of 6 to 14 carbon atoms, an ester, optionally unsaturated alkyl of 1 to 8 carbon atoms and optionally unsaturated cycloalkyl of 3 to 8 carbon atoms the latter two being optionally substituted with one or more halogen, R$_3$ is selected from the group consisting of hydrogen, alkyl of 1 to 3 carbon atoms, —CN and —C≡CH and A is the residue of an ACOOH pyrethrinoid acid having pesticidal properties.

51 Claims, No Drawings

PYRETHRINOIDS

STATE OF THE ART

Related prior art are commonly assigned U.S. Pat. No. 4,450,169 and Monsanto European patent application No. 64,353.

OBJECTS OF THE INVENTION

It is an object of the invention to provide the novel compounds of formula I and a novel process and intermediates for their preparation.

It is another object of the invention to provide novel pesticidal compositions and a novel method of combatting pests.

These and other objects and advantages of the invention will become obvious from the following detailed description.

THE INVENTION

The novel compound of the invention are A is selected from the group consisting of all stereoisomeric forms and mixtures thereof of a compound of the formula

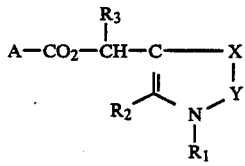

I wherein X is —O— or —S—, Y is —C=O,

or —CH$_2$—, R$_1$ is selected from the group consisting of hydrogen, halogen, optionally unsaturated alkyl of 1 to 8 carbon atoms and optionally unsaturated cycloalkyl of 3 to 8 carbon atoms, the latter two being optionally substituted with one or more halogen and aryl of 6 to 14 carbon atoms, R$_2$ is selected from the group consisting of hydrogen, —CF$_3$, —NO$_2$, —CN, halogen, alkoxy of 1 to 8 carbon atoms, aryl of 6 to 14 carbon atoms, an ester, optionally unsaturated alkyl of 1 to 8 carbon atoms and optionally unsaturated cycloalkyl of 3 to 8 carbon atoms, the latter two being optionally substituted with one or more halogen, R$_3$ is selected from the group consisting of hydrogen, alkyl of 1 to 3 carbon atoms, —CN and —C≡CH and A is the residue of an ACOOH pyrethrinoid acid.

The pyrethrinoid acid is an acid of the formula ACOOH wherein the acid is a biologically active pyrethrinoid acid of the art.

Examples of R$_1$ and R$_2$ are alkyl such as methyl, ethyl, n-propyl, isopropyl, n-butyl, isobutyl, tert.-butyl, n-pentyl, and n-hexyl; cycloalkyl such as cyclopropyl, cyclopropylmethyl, cyclobutyl, cyclopentyl and cyclohexyl; alkenyl such as allyl; alkynyl such as propargyl or butynyl; and aryl such as phenyl.

When R$_2$ is halogen, it is preferably methyl.

Among the preferred compounds of formula I are those wherein Y is C=O, those wherein R$_3$ is hydrogen, those wherein R$_1$ is alkenyl or alkynyl of 2 to 4 carbon atoms such as 2-propynyl or 2-propynyl and those wherein R$_2$ is —CF$_3$.

Among the preferred groups of A are those wherein A is selected from the group consisting of

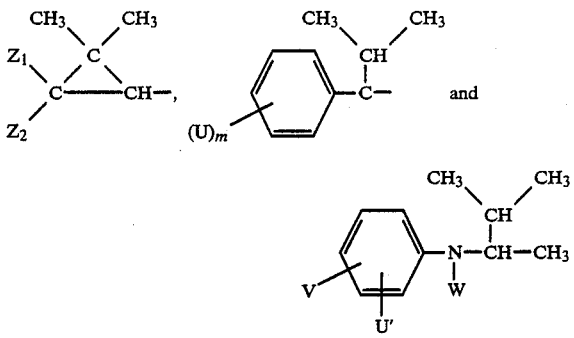

wherein Z$_1$ and Z$_2$ are methyl or Z$_1$ is hydrogen and Z$_2$ is selected from the group consisting of

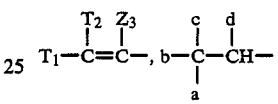

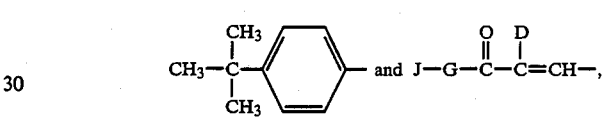

Z$_3$ is hydrogen or halogen, T$_1$ and T$_2$ are individually selected from the group consisting of hydrogen, halogen, —CF$_3$, —CN, phenyl optionally substituted with a halogen, and alkyl and alkoxy of 1 to 8 carbon atoms or taken together form

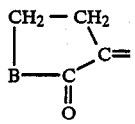

or taken together with the carbon to which are attached form a cycloalkyl of 3 to 6 carbon atoms, B is —O— or —S—, a,b,c and d are individually halogen, D is selected from the group consisting of hydrogen, halogen and alkoxy of 1 to 8 carbon atoms, G is —O— or —S—, J is selected from the group consisting of optionally unsaturated alkyl of 1 to 8 carbon atoms, optionally unsaturated cycloalkyl of 3 to 8 carbon atoms, these latter being optionally substituted with one or more halogens or one or more functional groups, aryl of 6 to 14 carbon atoms and a heterocycle, the latter two optionally substituted with one or more functional groups, U is selected from the group consisting of halogen and alkyl and alkoxy of 1 to 8 carbon atoms optionally substituted with one or more halogens, m is 0, 1 or 2 and if 2, the Us may be different U' and V are individually selected from the group consisting of hydrogen, halogen and —CF$_3$ and W is hydrogen or —CH$_3$.

When T$_1$, T$_2$ or Z$_3$ are halogen, it is preferably fluorine, bromine or chlorine. When T$_1$ or T$_2$ are alkyl or alkoxy, they are preferably methyl, ethyl, n-propyl, methoxy, ethoxy or n-propoxy, a,b,c and d are preferably chlorine or bromine and when D is halogen it is preferably fluorine, chlorine or bromine.

When J is alkyl of 1 to 8 carbon atoms substituted with at least one functional group, the alkyl may be methyl, ethyl, propyl, isopropyl, n-butyl, isobutyl, or tert-butyl, and the functional group is preferably one of those cited in the published European application No. 50,534. J may also be alkyl substituted by aryl, particularly by an optionally substituted phenyl radical.

When J is alkyl substituted by at least one functional group, J is preferably —$(CH_2)_{n1}$—$CHal_3$ in which $n_1$ is a whole number from 1 to 8 and Hal is a halogen, for example one of the following: —$CH_2$—$CCl_3$, —$CH_2$—$CF_3$, —$CH_2$—$CH_2$—$CCl_3$ or $CH_2$—$CH_2$—$CF_3$; —$(CH_2)_{n2}$—CH—$(Hal)_2$ in which Hal is defined as above and $n_2$ is a number from 0 to 8, for example —$CH_2$—$CHCl_2$, —$CH_2$—$CHF_2$ or —$CHF_2$; —$(CH_2)_{n1}$—$CH_2$Hal in which $n_1$ and Hal are defined as above, for example —$CH_2$—$CH_2$Cl or —$CH_2$—$CH_2$F; —C—$(CHal_3)_3$ in which Hal is defined as above, for example

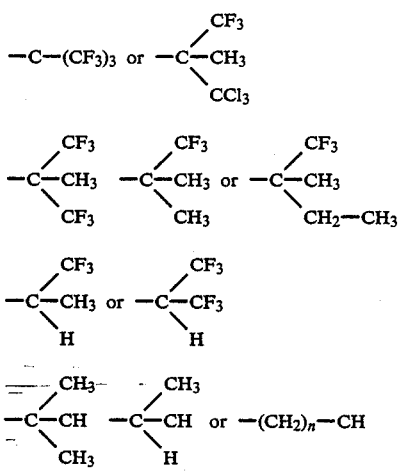

in which n is defined as previously;

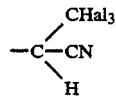

in which Hal is defined as previously, for example a radical is

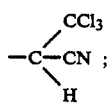

—$(CH_2)_{n1}$—$OR_a$ in which $n_1$ is defined as previously and $R_a$ is hydrogen or alkyl of 1 to 8 carbon atoms, for example —$CH_2$—O—$CH_3$, —$CH_2$—$CH_2$—O—$CH_3$, —$CH_2$—$CH_2$—O—$CH_2$—$CH_3$ or —$CH_2$—$CH_2$—OH;

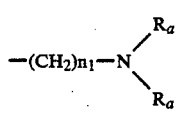

in which $n_1$ and $R_a$ are defined as previously and the two $R_a$ can be different from each other, for example

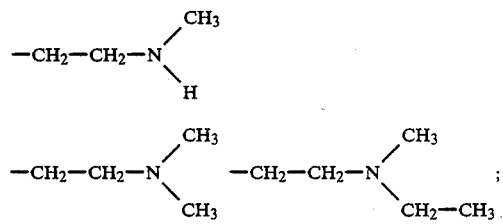

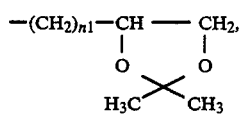

in which $n_1$ is defined as, for example

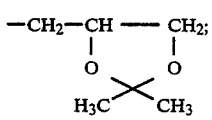

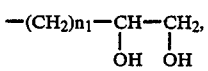

in which $n_1$ is defined as previously, for example

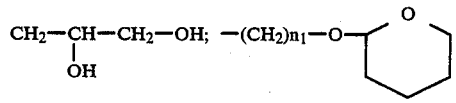

in which $n_1$ is defined as previously, for example

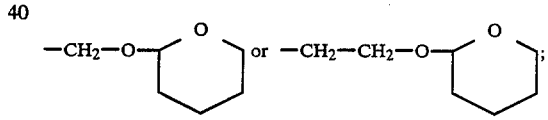

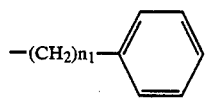

in which $n_1$ is defined as previously, for example benzyl or phenethyl;

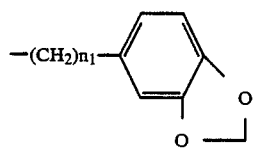

in which $n_1$ is defined as previously, for example,

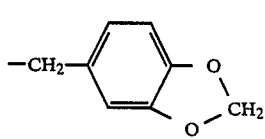

When J is optionally substituted aryl, it is preferably an optionally substituted phenyl. When J is a heterocyclic, it is preferably pyridyl, furyl, thienyl, oxazolyl or thiazolyl.

Among the preferred compounds of formula I are those wherein A is selected from the group consisting of

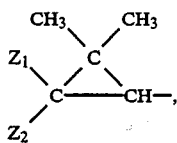 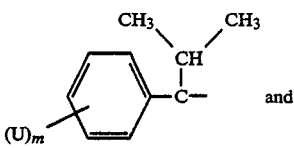 and

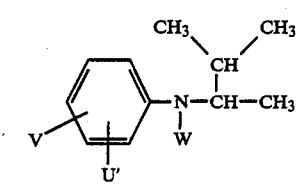

$Z_1$ and $Z_2$ are methyl or $Z_1$ is hydrogen and $Z_2$ is selected from the group consisting of

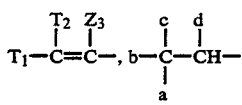

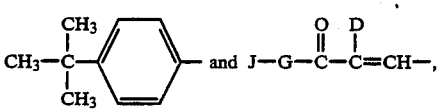

$Z_3$ is hydrogen or halogen, $T_1$ and $T_2$ are individually selected from the group consisting of hydrogen, halogen, —$CF_3$, —CN, phenyl optionally substituted with a halogen and alkyl and alkoxy of 1 to 8 carbon atoms or taken together form

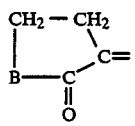

or taken together with the carbon to which they are attached form a cycloalkyl of 3 to 6 carbon atoms, B is —O— or —S—, a,b,c and d are individually halogen, D is selected from the group consisting of hydrogen, halogen and alkoxy of 1 to 8 carbon atoms, G is —O— or —S—, J is selected from the group consisting of optionally unsaturated alkyl or 1 to 8 carbon atoms, optionally unsaturated cycloalkyl of 3 to 8 carbon atoms, these latter being optionally substituted with one or more halogens or one or more functional group, aryl of 6 to 14 carbon atoms and a heterocycle, the latter two optionally substituted with one or more functional groups, U is selected from the group consisting of halogen and alkyl and alkoxy of 1 to 8 carbon atoms optionally substituted with one or more halogens, m is 0, 1 or 2 and if 2, the Us may be different U' and V are individually selected from the group consisting of hydrogen, halogen and —$CF_3$ and W is hydrogen of —$CH_3$.

More preferred compounds of formula I are those wherein A is

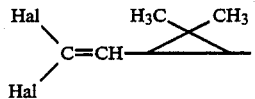

in all possible isomeric forms or in the form of mixtures of the stereoisomers, Hal is fluorine, bromine, chlorine or iodine and preferably bromine or

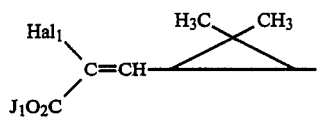

in all possible stereoisomeric forms, or in the form of mixtures of the stereoisomers, in which $Hal_1$ is halogen and $J_1$ is alkyl or cycloalkyl of up to 8 carbon atoms, optionally substituted at least by one halogen, the double bond having E geometry, for example those in which $Hal_1$ is fluorine or

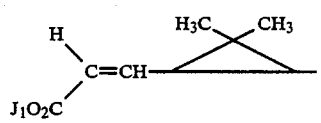

in all the possible stereoisomeric forms, or in the form of mixtures of these stereoisomers in which $J_1$ is defined as previously, the double bond having (Z) geometry and preferably $J_1$ is tert-butyl or

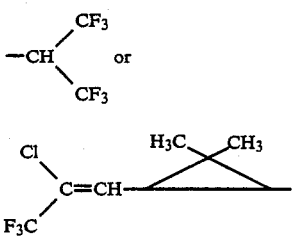

in all its possible stereoisomeric forms, or in the form of mixtures of the stereoisomers.

Specific preferred compounds of the invention are the products of Examples 7,8,11,23 and 25 as well as those of Examples 1,2,3,4,18 or 22.

The novel process of the invention for the preparation of a compound of formula I comprises reacting an alcohol of the formula

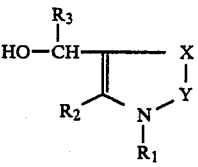 II in which X, Y, $R_1$, $R_2$ and $R_3$ have the above definitions with an acid of the formula

ACO$_2$H  III in which A has the above definition or a functional derivative of the acid. The functional derivative of the acid used is preferably an acid chloride.

When the acid of formula III and the alcohol of formula II are reacted together, the operation is preferably done in the presence of dicyclohexylcarbodiimide.

The compounds of formula II are new and may be prepared by the following reaction scheme

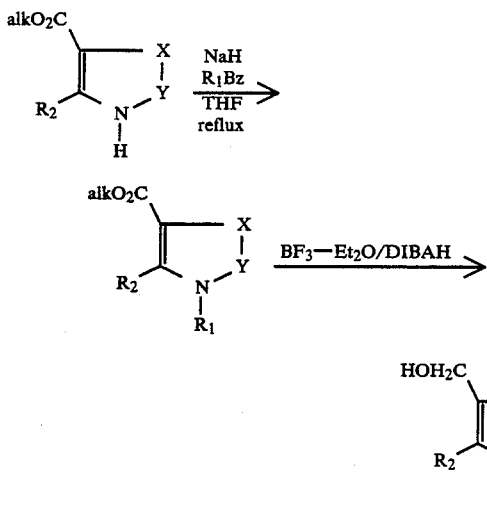

The preparation of some alcohols of formula II is given hereafter in the experimental part. The compounds of the formula

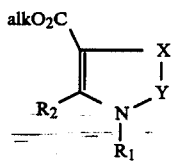

used as starting products are described for example in CA Vol. 92 110 998 P, Vol. 95 62 179 K, Vol. 97 182 393 P, Vol. 101 23 466 Z and in European patent No. EP 027020.

The novel pesticidal compositions of the invention are comprised of a pesticidally effective amount of at least one compound of formula I and an inert carrier. The compositions are useful to combat pests such as parasites of vegetables and of warm-blooded animals as well as parasites of premises and are particularly useful to combat insects, nematodes and parasitic acariens which attack warm-blooded animals and vegetables.

The compositions of the invention are particularly useful to combat insects in the agricultural field, for example, to control aphides and larvae of lepidoptera and coleoptera and are usually used at a dose of 10 to 300 g of the compounds of formula I per hectare. The compositions are also useful to combat insects in the premises for example to combat flies, mosquitoes and beetles.

Certain of the compounds of formula I posses an excellent lethal power and a very good knock-down power and the products of Examples 1, 11 and 21 are particularly remarkable on this point. The products of formula I have the advantages of being very photostable and not being toxic to mammals. The various properties of the compounds of formula I correspond perfectly to those required for modern agrochemical use permitting the protection of crops without damage to the environment.

The pesticidal compositions of the invention are useful to combat vegetable parasitic acariens and nematodes as well as to combat animal parasitic acariens such as ticks, especially ticks of Boophilus species, Hyalomnia species, Amblyomnia species and Rhipicephalus species and to combat all sorts of scabies such as sarcoptic scabies, psoroptic scabies and chorioptic scabies.

The invention also includes compositions intended to combat parasites of warm-blooded animals, parasites of premises and parasites of vegetables containing at least one compound of formula I.

For the compositions intended for premises or agricultural use, the compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula I.

In an advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 95% by weight, preferably.

In the case of a serpentine insecticide, the inert support may be made, for example, of pyrethrum marc, Tabu powder (or Machilus Thumbergii leaf powder), powder of pyrethrum stems, cedar needle powder, sawdust such as pine sawdust, starch, and powder of coconut shells. The active dose in this case is preferably 0.03 to 1% by weight.

The compositions of the invention for premises use may be prepared as a spraying oil containing the active ingredient and the oil may soak the wick of a lamp which is then subjected to combustion. The concentration of the compound of the invention in the oil is preferably 0.03 to 95% by weight.

The insecticidal compositions as well as the acaricidal and nematocidal compositions of the invention may also contain one or more other pesticides and are in the usual powder, granule, suspension, emulsion or solution form. For acaricide use, the compositions are preferably wettable powders for foliar spraying containing 1 to 80% of the active ingredient or liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2-propyl-4,5-methylene-dioxy-benzene (piperonyl butoxide) or N-(2-ethyl-heptyl)-bicyclo -[2,2-1]5-heptane-2,3- dicarboximide or piperonyl-bis-2(2'-n-butoxy-ethyl)-ethyl acetal (tropital).

When the compositions are to be used to combat parasitic acariens of animals, the active compounds of the invention are very often incorporated into alimentary compositions in association with a nutritive mixture adapted to the animal to be fed. The nutritive mixture will vary depending upon the specific animal but usually contains cereals, sugars and grains, soybean press cake, peanuts and turnsole, meal of animal origin such as fish meal, synthetic amino acids, mineral salts, vitamins and antioxidants.

The compositions of the invention show an excellent general tolerance and are equally useful as medicaments for treating affections created by ticks and scabies. The compositions may be used in veterinary and human medicines. In human medicine, the compositions may be used to combat lice as well as prevent or treat scabies. The compositions may also be used as anthelmintics.

The said medicaments may be administered externally by vaporization, by shampoo, by painting or by bathing. For veterinary usage, the compositions may also be administered by painting the dorsal spine by the "pour on" method as well as being administered digestively or parenterally.

The compositions of the invention are also useful as biocides or to regulate growth.

Another feature of the invention are insecticidal, acaricidal or nematocidal associations containing as an active ingredient at least one compound of formula I and as a second active ingredient at least one pyrethrinoid ester selected from the group consisting of esters of allethrolones, of 3,4,5,6-tetrahydrophthalimido-methyl alcohol, of 5-benzyl-3-furyl-methyl alcohol, of 3-phenoxy-benzyl alcohol and α-cyano-3-phenoxybenzyl alcohols with chrysanthemic acids, esters of 5-benzyl-3-furyl-methyl alcohol with 2,2-dimethyl-3-(2-oxo-3,4,5,6-tetrahydrothiophenylidene methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropyl-acetic acids, esters of allethrolone, 3,4,5,6-tetra hydrophthalimido-methyl alcohol, 5-benzyl-3-furyl-methyl alcohol, 3-phenoxy-benzyl alcohols or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the pyrethrinoid esters are in all possible stereoisomer forms.

The latter associated compositions of the invention are of particular interest for combatting by the polyvalence of their action, a large range of parasites or by manifesting a synergistic action in some cases.

The novel method of the invention for combatting parasites such as insects, nematodes and acariens comprises contacting the parasites with a pesticidally effective amount of at least one compound of formula I.

In the following examples there are described several preferred embodiments to illustrate the invention. However, it should be understood that the invention is not intended to be limited to the specific embodiments.

EXAMPLE 1

[2-oxo-3-(2-propynyl)-2,3-dihydro-4-trifluoromethyl-thiazol-5-yl]-methyl [1R [1α, 3α, (E)]] 2,2-dimethyl-3-[2-fluoro-3-oxo-3-(1,1-dimethylethoxy)-propenyl]-cyclopropane carboxylate

STEP A: Ethyl 2,3-dihydro-2-oxo-3-(2-propynyl)-4-trifluoromethyl-5-thiazolcarboxylate 6.9 g of ethyl 2,3-dihydro-2-oxo-4-trifluoromethyl-5-thiazole-carboxylate [prepared by the process of CA 92 110 998P] were dissolved in 70 ml of tetrahydrofuran at 0° ± 5° C. and then, 1.44 g of 50% sodium hydride in oil were added. Once the gaseous evolution ended, 15 ml of 2-bromopropyne were added and the mixture was refluxed for 48 hours. The mixture was poured on to an iced solution of monosodium phosphate and extraction was carried out with methylene chloride, then drying, filtering and concentrating under reduced pressure. The residue was chromatographed and elution with a hexane-ethyl acetate mixture (85-15) yielded 5.57 g of the expected product.

STEP B: 5-hydroxymethyl-3-(2-propynyl)-4-trifluoromethyl-2-(3H)-thiazolone (A) and 2,3-dihydro-3-(2-propynyl)-4-trifluoromethyl-5-thiazolmethanol (B)

1.9 ml of boron trifluoride etherate were added at −65° C. to a solution of 3.84 g of the product of Step A in 40 ml of toluene and the mixture was stirred for 30 minutes. Then, over about 90 minutes, 69 ml of a 1.2 molar solution of diisobutyl aluminium hydride in toluene were introduced at −65° C.±3° C. and the mixture was stirred for a further one hour at −70° C. The mixture was poured into an iced molar solution of potassium and sodium double tartrate and the mixture was stirred for 45 minutes, decanted and extracted with ethyl acetate. The extracts were washed with water, then with a saturated aqueous solution of sodium chloride. After drying and bringing to dryness, 2.7 g of resin were obtained which was chromatographed on silica and eluted with a hexane-isopropyl ether mixture (11) to obtain 1.85 g of the expected product (A) with an Rf=0.1, and 0.20 g of product (B) with an Rf=0.2.

STEP C: [2-oxo-3-(2-propynyl)-2,3-dihydro-4-trifluoromethyl-thiazol-5-yl]-methyl [1R-[1α, 3α, ΔE) 2,2-dimethyl-3-[2-fluoro-3-oxo-3-(1,1-dimethylethoxy)-propenyl]-cyclopropane carboxylate 0.12 g of 4-dimethylamino-pyridine and 0.78 g of dicyclohexylcarbodimide were added at 0°±5° C. to a solution of 0.7 g of [1R (1α, 3α, ΔE)]] 2,2-dimethyl-3-[2-fluoro-3-oxo-3-(1,1-dimethyl-ethoxy)-propenyl]-cyclopropane carboxylic acid and 0.94 g of the product of Step B and 15 m of methylene chloride and the mixture was allowed to return to ambient temperature. The mixture was stirred for one hour and after filtering, the filtrate was concentrated under reduced pressure at 40° C. The residue was chromatographed on silica and eluted with a hexane-ethyl acetate mixture (85-15) to obtain 1.1 g of the expected product with a specific rotation of [α]$_D$= +38.5°±2°(c=0.5% in CHCl$_3$).

Using the procedure of Example 1, the corresponding acids and alcohols were reacted to obtain the following products.

EXAMPLE 2

[2-oxo-3-(2-propynyl)-4-trifluoromethyl-2,3-dihydro-thiazol-5-yl]-methyl [1R [1α, 3α, ΔE]] 2,2-dimethyl-3-(2-fluoro-3-oxo-3-ethoxypropenyl)-cyclopropane carboxylate with a specific rotation of $[\alpha]_D = +36° \pm 2°$ (c=0.5% in CHCl$_3$).

EXAMPLE 3

[2-oxo-3-(2-propynyl)-4-trifluoromethyl-2,3-dihydro-thiazol-5-yl]-methyl [1R (1α, 3α)] 2,2-dimethyl-3-(2,2-dibromoethenyl)-cyclopropane carboxylate with a specific rotation of $[\alpha]_D = +14° \pm 1°$ (c=1% in CHCl$_3$) and melting at 68° C.

EXAMPLE 4

[2-oxo-3-(2-propynyl)-4-trifluoromethyl-2,3-dihydro-thiazol-5-yl]-methyl [1R [1α, 3α, ΔZ]] 2,2-dimethyl-3-[3-oxo-3-(1,1-dimethylethoxy)-1-propenyl]-cyclopropane carboxylate with a specific rotation of $[\alpha]_D = +67.5° \pm 2.5°$ (c=0.65% in CHCl$_3$).

EXAMPLE 5

[2-oxo-3-(2-propynyl)-4-trifluoromethyl-2,3-dihydro-thiazol-5-yl]-methyl 2,2,3,3-tetramethyl-cyclopropane carboxylate melting at <50° C.

EXAMPLE 6

[2-oxo-3-(2-propynyl)-4-trifluoromethyl-2,3-dihydro-thiazol-5-yl]-methyl [1S] [1-(4-chlorophenyl)-2-methyl-propyl-carboxylate with a specific rotation $[\alpha]_D = +5° \pm 2°$ (c=0.85% in toluene).

EXAMPLE 7

[2-oxo-3-(2-propynyl)-4-trifluoromethyl-2,3-dihydro-thiazol-5-yl]-methyl [1R, [1α, 3α, ΔZ]] 2,2-dimethyl-3-[2-chloro-3,3,3-trifluoro-propenyl]-cyclopropane carboxylate with a specific rotation of $[\alpha]_D = +35° \pm 2.5°$ (c=0.5% in CHCl$_3$).

EXAMPLE 8

[2-oxo-3-(2-propynyl)-4-trifluoromethyl-2,3-dihydro-thiazol-5-yl]-methyl [1R, [1α, 3α, ΔZ]] 2,2-dimethyl-3-[3-oxo-3-(1,1,1,3,3,3-hexafluoro-2-propyloxy)-1-propenyl]-cyclopropane carboxylate with a specific rotation of $[\alpha]_D = +33° \pm 2°$ (c=0.5% in CHCl$_3$).

EXAMPLE 9

[2-oxo-3-(2-propynyl)-4-trifluoromethyl-2,3-dihydro-thiazol-5-yl]-methyl [1R [1α, 3α, ΔZ]] 2,2-dimethyl-3-[2-chloro-2-(4-chlorophenyl)-ethenyl]-cyclopropane carboxylate with a specific rotation of $[\alpha]_D = +46° \pm 1.5°$ (c=0.9% CHCl$_3$).

EXAMPLE 10

[2,3-dihydro-2-oxo-3-(2-propynyl)-4-trifluoromethyl-oxazol-5-yl)]-methyl [1R, [1α, 3α, ΔE]] 2,2-dimethyl-3-[3-ethoxy-2-fluoro-3-oxo-propenyl]-cyclopropane carboxylate

STEP A: Ethyl 2,3-dihydro-2-oxo-3-(2-propynyl)-4-trifluoromethyl-oxazol-5-carboxylate 5.4 ml of diethyl azodicarboxylate were added at 10 C to a solution of 7 g of ethyl 2,3-dihydro-2-oxo-4-trifluoromethyl-oxazol-5-carboxylate [prepared as in Patent No. EP 027,020], 70 ml of tetrahydrofuran, 8.15 g of triphenylphosphine and 3.3 ml of propargyl alcohol and the mixture was stirred for one hour at 20° C. The mixture was poured into water and was extracted with ethyl acetate, dried, filtered and concentrated. The residue was chromatographed on silica and eluted with a hexane-ethyl acetate mixture (85-15) to obtain 4.6 g of the expected product melting at 72° C.

STEP B: 5-hydroxymethyl-3-(2-propynyl)-4-trifluoromethyl-2(3H)-oxazolone 520 mg of lithium aluminium hydride were introduced at −30° C. to a solution of 3.6 g of the product of Step A in 7.5 ml of ethyl ether and the mixture was poured into a solution of sodium and potassium double tartrate. The mixture was stirred for 16 hours and after decanting and extracting with ethyl acetate, the extracts were dried, filtered and concentrated. The residue was chromatographed on silica and eluted with a hexane-ethyl acetate mixture (7-3) to obtain 0.96 g of the expected product melting at 64° C.

STEP C: [2,3-dihydro-2-oxo-3-(2-propynyl)-4-trifluoromethyloxazol-5-yl]-methyl [1R, (1α, 3α, ΔE] 2,2-dimethyl-3-(3-ethoxy-2-fluoro-3-oxo-propenyl]-cyclopropane carboxylate Using the procedure of Step C of Example 1, the product of Step B was reacted to obtain the expected compound with a specific rotation of $[\alpha]_D = +13.5° \pm 2°$ (c=0.5% in CHCl$_3$).

EXAMPLE 11

[2,3-dihydro-2-oxo-3-(2-propynyl)-4-trifluoromethyl-oxazol-5-yl]-methyl [1R [1α, 3α, ΔE]] 2,2-dimethyl-3-(1,1-dimethylethoxy)-2-fluoro-3-oxo-propenyl]-cyclopropane-carboxylate with a specific rotation of $[\alpha]_D = +25° \pm 2°$ (c=0.6% in CHCl$_3$).

EXAMPLE 12

[2,3-dihydro-2-oxo-3-(2-propynyl)-4-trifluoromethyl-oxazol-5-yl]-methyl [1R (1α, 3α,)] 2,2-dimethyl-3-(2,2-dibromoethenyl)-cyclopropane carboxylate with a specific rotation of $[\alpha]_D = -6° \pm 1°$ C. (c=0.9% in CHCl$_3$) and melting at 74° C.

EXAMPLE 13

(2,3-dihydro-3-cyclopropylmethyl-2-oxo-4-trifluoromethyl-thiazol-5-yl)-methyl [1R (1α, 3α)] 2,2-dimethyl-3-(2,2-dibromoethenyl)-cyclopropane carboxylate

STEP A: Ethyl 2,3-dihydro-3-cyclopropylmethyl-2-oxo-4-tri-fluoro-methyl-thiazol-5-carboxylate 200 mg of 50% sodium hydride in oil were introduced at 0°+5° into a solution of 1 g of ethyl 2,3-dihydro-2-oxo-4-trifluoromethyl-5-thiazole carboxylate [CA Vol. 92 110 998P] and 10 ml of tetrahydrofuran and the mixture was stirred for half an hour at ambient temperature. Then 1 ml of bromoethyl cyclopropane and 0.63 g of sodium iodide were added and the mixture was stirred for one hour at ambient temperature and for one hour at 80° C. The mixture was allowed to return to ambient temperature was diluted with methylene chloride and poured over a solution of sodium acid phosphate. After extraction with methylene chloride, the extracts were dried, filtered and concentrated. The residue was chromatographed on silica and eluted with a hexane-ethyl acetate mixture (9-1) to obtain 1.03 g of the expected product with an Rf=0.25.

STEP B:
3-cyclopropylmethyl-5-hydroxymethyl-4-trifluoromethyl-2-(3H)-thiazolone 1.9 ml of boron trifluoride etherate were added at −65° C. to a solution of 4.05 g of the product of Step A in 40 ml of toluene. The mixture was stirred for half an hour at −65° C. and 70 ml of a 0.5M solution of aluminum diisobutyl hydride in toluene were introduced. The mixture was poured over 400 ml of a molar aqueous solution of sodium and potassium double tartrate and stirred for one hour. After decanting, extraction was carried out with ethyl acetate and the extracts were washed with water and dried. After filtering and concentrating, 3.5 g of a residue were obtained which was chromatographed on silica and eluted with a hexane-ethyl acetate mixture (7-3) to obtain 2.87 g of expected product with a Rf=0.25.

STEP C:

Using the procedure of Step C of Example 1, the product of Step B was reacted to obtain (2,3-dihydro-3-cyclopropylmethyl-2-oxo-4-trifluoromethyl-thiazol-5-yl]-methyl [1R (1α, 3α)] 2,2-dimethyl-3-(2,2-dibromoethenyl)-cyclopropane carboxylate with a specific rotation of $[\alpha]_D = +6°\pm2°$ (c=0.6% in CHCl$_3$).

EXAMPLE 14
(2,3-dihydro-3-cyclopropylmethyl-2-oxo-4-trifluoromethyl-thiazol-5-yl)-methyl [1R [1α, 3α, ΔE]] 2,2-dimethyl-3-(3-ethoxy-2-fluoro-3-oxo-propenyl)-cyclopropane carboxylate with a specific rotation of $[\alpha]_D = +33°\pm2°$ (c=0.6% in CHCl$_3$).

EXAMPLE 15
(3-cyclopropylmethyl-2,3-dihydro-2-oxo-4-trifluoromethyl-thiazol-5-yl)-methyl [1R [1α, 3α, ΔE]] 2,2-dimethyl-3-[3-(1,1-dimethyl ethoxy)-2-fluoro-3-oxo-propenyl]-cyclopropane-carboxylate with a specific rotation of $[\alpha]_D = +30.5°\pm2°$ (c=0.5% in CHCl$_3$).

EXAMPLE 16
[2,3-dihydro-2-oxo-3-(2-propenyl)-4-trifluoromethyl-thiazol-5-yl]-methyl [1R (1α, 3α)] 2,2-dimethyl-3-(2,2-dibromoethenyl)-cyclopropane carboxylate with a specific rotation of $[\alpha]_D = +7°\pm1.5°$ (c=0.7% in CHCl$_3$) and melting at 50° C.

EXAMPLE 17
[2,3-dihydro-2-oxo-3-(2-propenyl)-4-trifluoromethyl-thiazol-5-yl]-methyl [1R [1α, 3α, ΔE)]] 2,2-dimethyl-3-[3-ethoxy-2-fluoro-3-oxo-propenyl]-cyclopropane carboxylate with a specific rotation of $[\alpha]_D = +37.5°\pm1.5°$ (c=0.7% in CHCl$_3$)

EXAMPLE 18
[2,3-dihydro-2-oxo-3-(2-propenyl)-4-trifluoromethyl-thiazol-5-yl]-methyl [1R [1α, 3α, ΔE]] 2,2-dimethyl-3-[3-(1,1-dimethylethoxy)-2-fluoro-3-oxo-propenyl]-cyclopropane carboxylate.

STEP A: Ethyl 2,3-dihydro-2-oxo-3-(2-propenyl)-4-trifluoromethyl-thiazol-5-carboxylate 10 g of ethyl 2,3-dihydro-2-oxo-4-trifluoromethyl-5-thiazolcarboxylate (CA Vol. 92 110 998P), 200 ml of toluene, 2.6 g of potassium in pastilles, 6 ml of allyl bromide and 2.8 g of tetrabutylammonium bromide were heated at 90° C. for 3 hours and the mixture was allowed to return to ambient temperature followed by stirring for 2 hours. The mixture was washed with a N sodium hydroxide solution, with a N hydrochloric acid solution, with water and with a saturated sodium chloride solution. Drying, filtering and concentrating were carried out and the residue was chromatographed on silica and eluted with a hexane-ethyl acetate mixture (9-1) to obtain 8.65 g of the expected product with a Rf=0.25.

STEP B:
5-hydroxymethyl-3-(2-propenyl)-4-trifluoromethyl-2-(3H)-thiazolone 4.3 ml of boron trifluoride ethereate were introduced at −65° C. into a solution of 8.65 g of the product of Step A in 100 ml of toluene and the mixture was stirred at −65° C. Then, 155 ml of 0.5M solution of diisobutylaluminium hydride in toluene were introduced and the mixture was poured into an iced molar solution of sodium and potassium double tartrate followed by stirring for 2 hours. After decanting and extraction with ethyl acetate, the extracts were washed with water and with a saturated solution of sodium chloride, dried, filtered and concentrated. The residue was chromatographed on silica and elution with a hexane-ethyl acetate mixture (7-3) yielded 4 g of the expected product with a Rf=0.25.

STEP C:

Using the procedure of Step C of Example 1, the product of Step B was reacted to obtain [2,3-dihydro-2-oxo-3-(2-propenyl)-4-trifluoromethyl-thiazol-5-yl]-methyl [1R (1α, 3α, ΔE)] 2,2-dimethyl-3-[3-(1,1-dimethylethoxy)-2-fluoro-3-oxo-propenyl]-cyclopropane carboxylate with a specific rotation of $[\alpha]_D = +49°\pm1.5°$ (c=0.8% in CHCl$_3$).

EXAMPLE 19
[2-oxo-3-phenyl-4-trifluoromethyl-2,3-dihydro-thiazol-5-yl]-methyl [1R (1α, 3α, ΔE)] 2,2-dimethyl-3-(2-fluoro-3-oxo-3-ethoxy-1-propenyl)-cyclopropane carboxylate with a specific rotation of $[\alpha]_D = +41°\pm1°$ (c=1.2% in CHCl$_3$).

EXAMPLE 20
[2-oxo-3-phenyl-1-trifluoromethyl-2,3-dihydrothiazol-5-yl] methyl [1R (1α, 3α, ΔE)] 2,2-dimethyl-3-[2-fluoro-3-oxo-3-(1,1-dimethylethoxy)-1-propenyl]-cyclopropane carboxylate

STEP A: Ethyl 2-oxo-3-phenyl-4-hydroxy-4-trifluoromethyl-2,3,4,5-tetrahydrothiazol-5-yl-carboxylate 12.2 g of ethyl N-phenylthiocarbamate [(Ber. (1916) Vol. 49 p 1027)] and 14.7 g of ethyl trifluoroacetyl α-chloroacetate were dissolved in 300 ml of toluene and the mixture was refluxed with nitrogen bubbled in for 24 hours, then allowed to cool and distilled to dryness to obtain 22 g of the expected product.

STEP B:

The product of Step A was dissolved in 150 ml of methylene chloride and the mixture was cooled to 0° to 5° C. A solution of 11 ml of methane sulfonyl chloride and 40 ml of methylene chloride was added with stirring under a nitrogen atmosphere and then over 30 minutes, a solution of 18 ml of triethylamine in 30 ml of methylene chloride was added. The mixture was allowed to return to ambient temperature and stirred for 18 hours. Then, it was poured into a mixture of water and ice, decanted and extracted with methylene chloride. The extracts were washed, dried and brought to dryness to obtain 27 g of residue which was chromatographed on silica and eluted with a hexane-ethyl acetate mixture (9-1) to obtain 4.49 g of expected product melting at 55° C.

STEP C:
3-phenyl-4-trifluoromethyl-5-hydroxymethyl-2-(3H)-thiazolone.

0.5 ml of boron trifluoride ethereate were added at −65° C. to a solution of 1 g of the product of Step B in 20 ml of toluene and the mixture was stirred for 30 minutes. 20 ml of a 1.2M solution of diisobutyl aluminium hydride in toluene were added and the mixture was poured into a mixture of a solution of sodium and potassium tartrate with ice. The mixture was stirred for one hour, decanted and extracted with ethyl acetate. The extracts were washed with water, dried and brought to dryness. The residue was chromatographed on silica and elution with a hexane-ethyl acetate mixture (7-3) yielded 0.36 g of the expected product with a Rf=0.15 and melting at 135° C.

STEP D:

Using the procedure of Step C of Example 1, the product of Step C was reacted to obtain [2-oxo-3-phenyl-1-trifluoromethyl-2,3-dihydrothiazol-5-yl]-methyl [1R (1α, 3α, ΔE)] 2,2-dimethyl-3-[2-fluoro-3-oxo-3-(1,1-dimethylethoxy)-1-propenyl]-cyclopropane carboxylate with a specific rotation of $[\alpha]_D = +48° \pm 2°$ (c=0.5% in CHCl$_3$).

EXAMPLE 21

[2-oxo-3-(2-propynyl)-2,3-dihydrothiazol-5-yl]-methyl [1R (1α, 3α,)] 2,2-dimethyl-3-(2,2-dibromoethenyl)-cyclopropane carboxylate with a specific rotation of $[\alpha]_D = +14.5° \pm 0.5°$ (c=1.4% in CHCl$_3$) and melting at 107°–108° C.

EXAMPLE 22

[2-oxo-3-(2-propynyl)-2,3-dihydrothiazol-5-yl]-methyl [1R (1α, 3α, ΔE)]] 2,2-dimethyl-3-(2-fluoro-3-oxo-3-ethoxy-1-propenyl)-cyclopropane carboxylate with a specific rotation of $[\alpha]_D = +47° \pm 1.5°$ (c=0.8% in CHCl$_3$).

EXAMPLE 23

[2-oxo-3-(2-propynyl)-2,3-dihydrothiazol-5-yl]-methyl [1R (1α, 3α, ΔE)]] 2,2-dimethyl-3-(2-fluoro-3-oxo-3-(2,2-dimethyl-ethoxy)-1-propenyl]-cyclopropane carboxylate

STEP A: Ethyl (2-oxo-2,3-dihydrothiazol-5-yl)-carboxylate 50 ml of dichloroethane were added to a mixture of 8.25 g of ethyl formyl chloroacetate and 5.25 g of ethyl thiacarbamate and the mixture was refluxed for 4 hours with nitrogen bubbled in. After evaporation to dryness, the residue was dissolved in 5 ml of tepid isopropyl ether and crystallization was started and allowed for about 16 hours at +5° C. After separating, washing and drying, 2.44 g of the expected product melting at 127° C. were obtained.

STEP B: Ethyl [2,3-dihydro-2-oxo-3-(2-propynyl)-thiazol-5-yl]-carboxylate

A mixture of 8.65 g of the product of Step A in 130 ml of toluene, 2.8 g of potassium hydroxide, 4.5 ml of 3-bromo-1-propane and 1.66 g of tetrabutyl ammonium bromide was heated to 95 C and stirred for 3 hours. The mixture was decanted, washed with N sodium hydroxide, with N hydrochloric acid and with water saturated with sodium chloride, dried and brought to dryness. The residue was chromatographed and elution with a hexane-chloroform-acetone mixture (70-15-15) yielded 4.74 g of the expected product melting at 70° to 71° C.

STEP C: 3-(2-propynyl)-5-hydroxymethyl-2-(3H)-thiazolone

A solution of 8.44 g of the product of Step B in 100 ml of toluene was cooled to −65° C. to −70° C. and 5.6 g of boron trifluoride etherate were added. The mixture was stirred for 30 minutes and 200 ml of a 1.2M solution of diisobutyl aluminium hydride in toluene were introduced over 2 hours 15 minutes. Stirring was carried out for a further 30 minutes and the mixture was poured into 1.5 l of a M solution of potassium and sodium tartrate. After stirring for one hour and decanting, extraction was carried out with ethyl acetate. The extracts were washed with water saturated with sodium chloride, dried and brought to dryness. The residue was chromatographed and elution with a hexane-chloroform-acetone mixture (6-2-2) yielded. 2.33 g of the expected product melting at 97° to 98° C.

STEP D:
[2-oxo-3-(2-propynyl)-2,3-dihydro-thiazol-5-yl]-methyl [1R 1α, 3αΔE// 2,2-dimethyl-3-/2-fluoro-3-oxo-3-(2,2-dimethylethoxy)-1-propenyl/ cyclopropane carboxylate.

Using the procedure of Step C of Example 1, the product of Step C was reacted to obtain the expected product with a specific rotation $[\alpha]_D = +52° \pm 2°$ (c=0.5% in CHCl$_3$).

EXAMPLE 24

[2-oxo-3-(2-propynyl)-4-methyl-2,3-dihydrothiazol-5-yl]-methyl [1R (1α, 3α)] 2,2-dimethyl-3-(2,2-dibromoethenyl)-cyclopropane-carboxylate.

STEP A: Ethyl [2,3-dihydro-2-oxo-3-(2-propynyl)-4-methylthiazol-5-yl]-carboxylate A solution of 19.4 g of ethyl β-amino-crotonate and 40 ml of chlorobenzene was cooled to 5° C. and 23.2 g of chlorothio chloroformyl chloride were introduced over 20 minutes. The mixture was allowed to return to ambient temperature, and maintained at this temperature for one hour, then heated to 80° C. for 4 hours. The mixture was cooled, filtered, washed with petroleum ether and dried to obtain 19.9 g of the expected product melting at 180° C. after crystallization from ethanol.

STEP B: Ethyl [2,3-dihydro-2-oxo-3-(2-propynyl)-4-methylthiazol-5-yl]-carboxylate 20.6 g of the product of Step A in 300 ml of toluene, 6.2 g of potassium hydroxide in pastilles, 10.4 ml of 3-bromo-1-propyne and 3.65 g of tetrabutylammonium bromide were stirred under an inert atmosphere and the mixture was heated at 95° C. for 19 hours, then allowed to return to ambient temperature. After decanting, the organic phase was washed with N sodium hydroxide, with hydrochloric acid, with water, then with water saturated with sodium chloride, dried and evaporated to dryness. The residue was chromatographed on silica and eluted with a hexane-chloroform-acetone mixture (8-1-1) to obtain 16.4 g of the expected product melting at 65° C.

STEP C: 3-(2-propynyl)-4-methyl-5-hydroxymethyl-2-(3H)thiazolone

Using the procedure of Step C of Example 21, 2.25 g of the product of Step B were reacted to obtain 1.03 g of the expected product melting at 62° C.

STEP D:

Using the procedure of Step C of Example 1, the product of Step C was reacted to obtain [2-oxo-3-(2-propynyl)-2,3-dihydrothiazol-5-yl]-methyl [1R (1α, 3α)] 2,2-dimethyl-3-(2,2-dibromoethenyl)-cyclopropane carboxylate with a specific rotation of $[\alpha]_D = -2° \pm 2°$ (c=0.5% in CHCl$_3$).

EXAMPLE 25

[2-oxo-3-(2-propynyl)-4-methyl-2,3-dihydrothiazol-5-yl]-methyl [1R [1α, 3α, ΔE]] 2,2-dimethyl-3-(2-fluoro-3-oxo-3-ethoxy-propenyl)-cyclopropane carboxylate with a specific rotation of $[\alpha]_D = +38° \pm 2°$ (c=0.55% in CHCl$_3$).

EXAMPLE 26

[2-oxo-3-(2-propynyl)-4-methyl-2,3-dihydrothiazol-5-yl]-methyl [1R [1α, 3α, ΔE]] 2,2-dimethyl-3-[2-fluoro-3-oxo-3-(1,1-dimethylethoxy)-1-propenyl]-cyclopropane carboxylate with a specific rotation $[\alpha]_D = +46° \pm 2°$ (c=0.6% in CHCl$_3$)

EXAMPLE 27

[2-oxo-3-benzyl-4-trifluoromethyl-2,3-dihydrothiazol-5-yl]-methyl [1R (1, 3)] 2,2-dimethyl-3-(2,2-dibromoethenyl)-cyclopropane carboxylate

STEP A: Ethyl [2,3-dihydro-2-oxo-3-benzyl-4-trifluoromethylthiazol-5-yl]-carboxylate 5 g of ethyl (2,3-dihydro-2-oxo-4-trifluoromethyl-thiazol-5-yl)-carboxylate (CA Vol. 92 110 998P), 80 ml of toluene, 1.16 g of potassium hydroxide, 3.7 ml of benzyl bromide and 1.61 g of tetrabutyl-ammonium bromide were heated at 70° C. for 7 hours and the mixture was allowed to return to ambient temperature, and was decanted, washed and dried to obtain 7.2 g of product which was chromatographed on silica. Elution with a hexane-isopropyl ether mixture (8-2) yielded 5.46 g of the expected product with a Rf=0.17.

STEP B: 3-benzyl-4-trifluoromethyl-5-hydroxymethyl-2-(3H)-thiazolone 3.13 g of the product of Step A, 30 ml of toluene and 1.3 ml of boron trifluoride etherate were stirred for 30 minutes at −65° to −70° C. and 48 ml of 1.2M solution of diisobutyl aluminium hydride in toluene were added over 2 hours. The mixture was poured into an iced molar solution of sodium and potassium tartrate and after stirring for one hour and decanting, extraction was carried out with ethyl acetate. The extracts were washed, dried and brought to dryness and the residue was chromatographed on silica. Elution with a hexaneisopropyl ether mixture (1-1) yielded 2.16 g of the expected product with a Rf=0.1.

STEP C:

Using the procedure of Step C of Example 1, the product of Step B was reacted to obtain [2-oxo-3-benzyl-4-trifluoromethyl-2,3-dihydro-thiazol-5-yl]-methyl [1R (1α, 3α,] 2,2-dimethyl-3-(2,2-dibromoethenyl)-cyclopropane carboxylate with a specific rotation of $[\alpha]_D = +7.5° \pm 1°$ (c=0.85% in CHCl$_3$) and melting at 70° C.

EXAMPLE 28

[2-oxo-3-benzyl-4-trifluoromethyl-2,3-dihydro-thiazol-5-yl]-methyl [1R [1α, 3α, ΔE] 2,2-dimethyl-3-(2-fluoro-3-oxo-3-ethoxy-1-propenyl)-cyclopropane carboxylate with a Rf=0.22 [silica eluent: hexane-isopropyl ether (1-1)] and a specific rotation of $[\alpha]_D = +37° \pm 1°$ (c=1% in CHCl$_3$).

EXAMPLE 29

[2-oxo-3-benzyl-4-trifluoromethyl-2,3-dihydro-thiazol-5-yl]-methyl [1R [1α, 3α, ΔE]] 2,2-dimethyl-3-[(2-fluoro-3-oxo-3-(1,1-dimethylethoxy)-1-propenyl)]-cyclopropane carboxylate with a specific rotation of $[\alpha]_D = +41° \pm 2°$ (c=0.7% in CHCl$_3$).

EXAMPLE 30

[2-oxo-3-(2-propynyl)-4-trifluoromethyl-2,3-dihydro-thiazol-5-yl]-prop-2-ynyl [1R [1α, (RS), 3α, Δ(E)]] 2,2-dimethyl-3-[2-fluoro-3-oxo-3-ethoxy-1-propenyl]-cyclopropane-carboxylate

STEP A: [2-oxo-3-(2-propynyl)-4-trifluoromethyl-2,3-dihydro-thiazol-5-yl]-carboxaldehyde A mixture of 4 g of 2,3-dihydro-2-oxo-3-(2-propynyl)-4-trifluoromethyl-5-thiazole methanol, 60 ml of methylene chloride and 8 g of manganese dioxide was stirred for 7½ hours and then the mixture was stirred for another 29 hours. After filtering and rinsing with methylene chloride, the filtrate was evaporated to dryness. The residue was chromatographed on silica and eluted with a hexane-isopropyl ether mixture (1-1) to obtain 3.48 g of the expected product melting at 58° to 59° C.

STEP B: [3-(2-propynyl)-4-trifluoromethyl-5-(1-hydroxy-prop-2-ynyl)-2-(3H)-thiazolone]

A solution of 1.17 g of the product of Step A and 7.5 ml of tetrahydrofuran was added to 18.75 ml of a 0.8M solution of ethynyl magnesium bromide in tetrahydrofuran and the mixture was stirred for one hour at 0° to 5° C. Then the mixture was poured into a solution of monosodium phosphate, decanted, and extracted with ethyl acetate. The extracts were washed with water, and with water saturated with sodium chloride and evaporated to dryness. The residue was chromatographed on silica and eluted with a hexane-isopropyl ether mixture (1-1) to obtain 1.13 g of the expected product with a Rf=0.15.

STEP C:

Using the procedure of Step C of Example 1, the product of Step B was reacted to obtain [2-oxo-3-(2-propynyl)-4-trifluoromethyl-2,3-dihydro-thiazol-5-yl]-prop-2-ynyl [1R (1α, (RS), 3α, E] 2,2-dimethyl-3-[2-fluoro-3-oxo-3-ethoxy-1-propenyl]-cyclopropane carboxylate with a specific rotation of $[\alpha]_D = +29.5° \pm 2°$ (c=0.6% in CHCl$_3$).

EXAMPLE 31

[2-oxo-3-(2-propynyl)-4-trifluoromethyl-2,3-dihydro-thiazol-5-yl]-prop-2-ynyl [1R [1α, (RS), 3α, ΔE]] 2,2-dimethyl-3-[2-fluoro-3-oxo-3-(1,1-dimethyl-ethoxy)-1-propenyl]-cyclopropane carboxylate with a specific rotation of $[\alpha]_D = +38° \pm 2.5°$ (c=0.5% in CHCl$_3$).

EXAMPLE 32

[2-oxo-3-(2-propynyl)-4-trifluoromethyl-2,3-dihydro-thiazol-5-yl]-ethyl [1R [1α, (RS) 3α, ΔE]] 2,2-dimethyl-3-[2-fluoro-3-oxo-3-(1,1-dimethylethoxy)-1-propenyl]-cyclopropane carboxylate STEP A: (RS) 3-(2-propynyl)-4-trifluoromethyl-5-(1-hydroxyethyl)-2 (3H)-thiazolone 30 ml of a 1M solution of methyl magnesium iodide in ethyl ether, 2.35 g of [2-oxo-3-(2-propynyl)-4-trifluoromethyl-2,3-dihydrothiazol-5-yl]-carboxaldehyde and 12 ml of tetrahydrofuran were mixed together and the suspension was stirred for 40 minutes. A saturated aqueous solution of monosodium phosphate was added, and the mixture was poured into a mixture of water, ice and ethyl ether. After decanting and extracting with ethyl ether, the extracts were washed, dried and brought to dryness. The 2.7 g of residue were chromatographed on silica and eluted with a hexane-isopropyl ether mixture (7-3) to obtain 1.87 g of the expected product melting at 77° to 78° C.

STEP B:

Using the procedure of Step C of Example 1, the product of Step A was reacted to obtain [2-oxo-3-(2-propynyl)-4-trifluoromethyl-2,3-dihydro-thiazol-5-yl]-ethyl [1R (1α, (RS), 3α, ΔE)] 2,2-dimethyl-3-[2-fluoro-3-oxo-3-(1,1-dimethylethoxy)-1-propenyl] cyclopropane carboxylate with a specific rotation of $[\alpha]_d = +53° \pm 2.5°$ (c=0.5% in CHCl$_3$).

EXAMPLE 33

[2-oxo-3-(2-propynyl)-4-trifluoromethyl-2,3-dihydro-thiazol-5-yl] ethyl [1R [1α, (RS), 3α, ΔE//2,2-dimethyl-3-(2-fluoro-3-oxo-3-ethoxy-1-propenyl)-cyclopropane carboxylate with a specific rotation of $[\alpha]_D = +45° \pm 2°$ (c=0.7% in CHCl$_3$).

EXAMPLE 34

[3-(2-propynyl)-4-trifluoromethyl-2,3-dihydro-thiazol-5-yl]-methyl [1R [1α, 3α, ΔE]] 2,2-dimethyl-3-[3-ethoxy-2-fluoro-3-oxo-1-propenyl]-cyclopropane carboxylate with a specific rotation of $[\alpha]_D = +25° \pm 2°$ (c=0.5% in toluene).

EXAMPLE 35

[3-(2-propynyl)-4-trifluoromethyl-2,3-dihydro-thiazol-5-yl]-methyl [1R [1α, 3α, ΔE]] 2,2-dimethyl-3-[2-fluoro-3-(1,1-dimethyl-ethoxy)-3-oxo-1-propenyl]-cyclopropane carboxylate Chromatography is carried out on silica, eluting with a hexane-ethyl acetate mixture (8-2) for a Rf=0.35.

The starting alcohol of the 2 previous products, 2,3-dihydro-3-(2-propynyl)-4-trifluoromethyl-5-thiazol methanol, was product B, of Step B of Example 1.

EXAMPLE 36

[2-oxo-3-(2-propynyl)-4-trifluoromethyl-2,3-dihydro-thiazol-5-yl]-methyl [1R [1α, 3α, ΔZ]] 3-(2-cyano-2-methoxyethenyl)-2,2-dimethylcyclopropane carboxylate with a specific rotation of $[\alpha]_D = +31° \pm 2°$ (c=0.7% in toluene).

EXAMPLE 37

[2-oxo-3-(2-propynyl)-4-trifluoromethyl-2,3-dihydro-thiazol-5-yl]-methyl [1R trans] 2,2-dimethyl-3-(3-t-butyl-phenyl)-cyclopropane carboxylate with a Rf=0.13 (silica/hexane-ethyl acetate 1-1).

The starting alcohol was product A of Step B of Example 1.

EXAMPLE 38

[3-(2-butynyl)-2-oxo-4-trifluoromethyl-2,3-dihydro-thiazol-5-yl]-methyl [1R (1α, 3α,)] 3-(2,2-dibromoethenyl) 2,2-dimethyl cyclopropane carboxylate STEP A: Ethyl 5-[3-(2-butynyl)-2-oxo-4-trifluoromethyl-2,3-dihydro-thiazolyl]-carboxylate 6.54 g of ethyl 2,3-dihydro-2-oxo-4-trifluoromethyl-5-thiazol carboxylate, 150 ml of tetrahydrofuran, 6.52 g of triphenyl phospine and 3.5 ml of butyn-2-yl-1 alcohol were mixed together and 6.15 ml of diethyl azodicarboxylate in 50 ml of tetrahydrofuran were added over one hour at +10° C., +15° C. The mixture was stirred for 20 hours at 20° C., poured over ice, and extracted with ethyl acetate. The organic phase was dried and evaporated to dryness and the residue was chromatographed on silica. Elution with a flugene(trichloro trifluoroethane)-diisopropyl oxide mixture (8-2) yielded 3.95 g of the expected product.

IR Spectrum (CHCl$_3$):
absorption of 1738 and 1685 cm$^{-1}$ (C=O), 1590 cm$^{-1}$ (C=C) and 2245 cm$^{-1}$ (C≡C).

STEP B:
[2-oxo-3-(2-butynyl)-4-trifluoromethyl-2,3-dihydro-thiazol-5-yl]-methyl alcohol.

35 ml of diisobutylaluminium hydride (1.2M in toluene), 7 ml of toluene and 16 ml of hexane were mixed together, cooled to −5° C. to 0° C. and over 15 minutes, 26 ml of butyllithium at 15% in hexane were added. The mixture was stirred at 0° C. for one hour, then cooled to −65° C. 3.9 g of the product of Step A in 25 ml of toluene were added over 20 minutes to 54 ml of the said solution. After stirring for 3 hours at −65° C., 0.35 g of sodium borohydride in solution in 25 ml of ethanol were added over 10 minutes. The mixture was stirred for 45 minutes allowing the temperature to rise, and was then poured over 100 g of ice and 100 ml of a 1M aqueous solution of sodium and potassium double tartrate. After stirring for one hour and extraction with ethyl ether, the organic phase was dried and concentrated to dryness to obtain 3.3 g of the expected product.

IR Spectrum (CHCl$_3$)
absorption at 1672 cm$^{-1}$ (C=O), 3613 cm$^{-1}$ (—OH) and 2240 cm$^{-1}$ (C≡C).

STEP C

Using the procedure of Step C of Example 1, the product of Step B was reacted to obtain [3-(2-butynyl)-2-oxo-4-trifluoromethyl-2,3-dihydro-thiazol-5-yl]-methyl [1R (1α, 3α)] 2,2-dimethyl-3-(2,2-dibromoethenyl)-cyclopropane carboxylate with a specific rotation of $[\alpha]_D = +10° \pm 2°$ (c=0.5% in toluene).

EXAMPLE 39

[3-(2-butynyl)-2-oxo-4-trifluoromethyl-2,3-dihyrothiazol-5-yl]-methyl [1R, 1α, 3α, ΔE] 2,2-dimethyl-3-[2-fluoro-3-(1,1-dimethylethoxy)-3-oxo-1-propenyl]-cyclopropane carboxylate with a specific rotation of= +49° ±2.5° (c=0.5% in toluene).

EXAMPLE 40

[3-(2-butynyl)-2-oxo-4-trifluoromethyl-2,3-dihydro-thiazol-5-yl]-methyl [1R, 1α, 3α, ΔE] 2,2-dimethyl-3-[3-ethoxy-2-fluoro-3-oxo-1-propenyl]-cyclopropane carboxylate with a specific rotation of $[\alpha]_D = +49.5° \pm 2.5°$ (c=0.6% in toluene).

EXAMPLE 41

[3-(3,3-dichloro-2-propenyl)-2-oxo-4-trifluoromethyl-2,3-dihydro-thiazol-5-yl]-methyl [1R, 1α, 3α, ΔE] 2,2-dimethyl-3-[2-fluoro-3-(1,1-dimethylethoxy)-3-oxo-1-propenyl]-cyclopropane carboxylate STEP A: Ethyl 5-[3-(3,3-dichloro-2-propenyl)-2-oxo-4-trifluoromethyl-2,3-dihydrothiazolyl]-carboxylate 6 g of ethyl 2,3-dihydro-2-oxo-4-trifluoromethyl-5-thiazol carboxylate and 30 ml of dimethylformamide were mixed together and 1.27 g of sodium hydride (at 50% in oil) were added. The mixture was stirred for 15 minutes and a solution of 5.78 g of 1,1-dichloro-3-bromo-1-propene in 10 ml of dimethylformamide was then introduced at +5° C. over 10 minutes. The mixture was stirred for 45 minutes at +5° C. and then at 20° C. for 67 hours. The mixture was poured into an aqueous solution of monosodium phosphate, then extracted with isopropyl ether. The organic phase was dried and the solvent was evaporated. The residue was chromatographed on silica and eluted with a hexane-ethyl acetate mixture (9-1) to obtain 8.7 g of the expected product.

IR Spectrum: (CHCl$_3$):
absorption at 1738 and 1685 cm$^{-1}$ (C=O), 1597 and 1628 cm$^{-1}$ (C=C).

STEP B:

[3-(3,3-dichloro-2-propenyl)-2-oxo-4-trifluoromethyl-2,3-dihydrothiazol-5-yl]-methyl alcohol Using the procedure of Step B of Example 38, 4.35 g of the product of Step A were reacted to obtain 3.61 g of the expected product melting at 81° C.

STEP C:

Using the procedure of Step C of Example 1, the product of Step C was reacted to obtain [3-(3,3-dichloro-2-propenyl]-2-oxo-4-trifluoromethyl-2,3-dihydro-thiazol-5-yl]-methyl [1R, 1α, 3α, ΔE] 2,2-dimethyl-3-[2-fluoro-3-[1,1-dimethylethoxy)-3-oxo-1-propenyl]-cyclopropane carboxylate with a specific rotation of $[\alpha]_D = +55.5° \pm 2°$ (c=0.7% in toluene).

EXAMPLE 42

[3-(3,3-dichloro-2-propenyl)-2-oxo-4-trifluoromethyl-2,3-dihydro-thiazol-5-yl]-methyl [1R, 1α, 3α, ΔE] 2,2-dimethyl-3-(3-ethoxy-2-fluoro-3-oxo-1-propenyl]-cyclopropane carboxylate with a specific rotation of $[\alpha]_D = +53.5° \pm 2.5°$ (c=0.5% in toluene).

EXAMPLE 43

[3-[(3,3-dichloro-2-propenyl)-2-oxo-4-trifluoromethyl-yl-2,3-dihydro-thiazol-5-yl]-methyl [1R, (1α, 3α)] 3-(2,2-dibromoethenyl)-2,2-dimethyl cyclopropane carboxylate with a specific rotation of $[\alpha]_D = +23.5° \pm 1.5°$ (c=1% in toluene) and melting at 66° C.

EXAMPLE 44

A soluble concentrate was prepared containing 0.25 g of the product of Example 2, 1.00 g of piperonyl butoxide, 0.25 g of Tween 80, 0.1 g of Topanol A and 98.4 g of water.

EXAMPLE 45

An emulsifiable concentrate was prepared by intimately mixing 0.015 g of the product of Example 3, 0.5 g of piperonyl butoxide, 0.1 g of Topanol A, 3.5 g of Tween 80 and 95.885 g of xylene.

EXAMPLE 46

An emulsifiable concentrate was prepared by homogeneously mixing 1.5 g of the product of Example 11, 20.00 g of Tween 80, 0.1 g of Topanol A and 78.4 g of xylene.

EXAMPLE 47

A fumigant composition was prepared by homogeneously mixing 0.25 g of the product of Example 10, 25.00 g of Tabu powder, 40.00 g of Cedar leaf powder, 33.75 g of pine wood sawdust and 0.5 g of both brilliant green and p-nitrophenol.

BIOLOGICAL DATA (1) Study of the Knockdown activity on the common fly

The insects were 4-day old female common flies and the operation was carried out by direct spraying in a Kearns and March chamber, using as a solvent a mixture of acetone (5%) and Isopar L (petroleum solvent) (quantity of solvent used: 2 ml per second). 50 insects per treatment were used and readings were made every minute up to 10 minutes, then after 15 minutes, and the KT$_{50}$ was determined by the usual methods. The results are in the following Table.

TABLE I

| Compound of example | KT50 (in mn) concentration at 0.1 g/l |
|---|---|
| 1 | 5.5 |
| 2 | 2.25 |
| 3 | 2.45 |
| 7 | 3.5 |
| 10 | 3.1 |
| 11 | 2.6 |
| 17 | 2.9 |
| 18 | 7.6 |
| 22 | 2.14 |
| 23 | 1.52 |

TABLE I-continued

| Compound of example | KT50 (in mn) concentration at 0.1 g/l |
| --- | --- |
| 24 | 5.6 |
| 25 | 1.16 |
| 34 | 5.7 |
| 36 | 4.88 |

CONCLUSION

The products of the invention are endowed with a very good knockdown effect on common flies.

(2) Activity of Tetranychus urticae. Adulticide test

Bean plants having two cotyledonary leaves were treated with an acetone solution of the product using a Fisher gun. After drying, 25 females of the acarida Tetranychus urticae per leaf were positioned, that is 50 individuals per experimental dose per plant. A check for the effectiveness was carried out after 80 hours of contact and the $LC_{50}$ was measured in mg/hl.

TABLE II

| Example | LC50 |
| --- | --- |
| 1 | 75 |
| 4 | 44 |
| 7 | 31 |
| 8 | 30 |
| 11 | 29 |
| 18 | 75 |
| 30 | 96 |

CONCLUSION

The products of the invention are endowed with a remarkable acaricide effect on Tetranychus urticae.

(3) Study of the lethal effect on Aphis cracivora 7 day old adults and 10 aphides per concentration used were employed and a contact-injection method was used. The treatment was carried out with a Fisher gun on a bean leaf which was placed in a Petri dish made of plastic on a moistened circular piece of paper. The treatment was carried out with 2 ml of acetone solution of the product under test (1 ml per side of leaf) and infestation by the insect was effected after the leaf had dried. The insects were maintained in contact with the leaf for one hour and then the insects were placed on leaves which were untreated and the mortality was checked after 24 hours. The experimental results are summarized in the following table:

TABLE III

| Compound | LC50 in mg/liter |
| --- | --- |
| 1 | 1.98 |
| 3 | 1.3 |
| 7 | 0.8 |
| 8 | 0.35 |
| 18 | 0.95 |

Various modifications of the compounds and the method of the invention may be made without departing from the spirit or scope thereof and it is to be understood that the invention is intended to be limited only as defined in the appended claims.

What we claim is:

1. All stereoisomeric forms and mixtures thereof of a compound of the formula

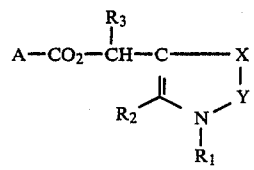

wherein X is —S—, Y is C=O, $R_1$ is selected from the group consisting of hydrogen, halogen, saturated, or unsaturated alkyl of 1 to 8 carbon atoms and saturated or unsaturated cycloalkyl of 3 to 8 carbon atoms, the latter two being unsubstituted or substituted with at least one halogen and aryl of 6 to 14 carbon atoms, $R_2$ is selected from the group consisting of hydrogen, —$CF_3$, —$NO_2$, —CN, halogen, alkoxy of 1 to 8 carbon atoms, aryl of 6 to 14 carbon atoms, saturated or unsaturated alkyl of 1 to 8 carbon atoms, saturated or unsaturated cycloalkyl of 3 to 8 carbon atoms, the latter two being unsubstituted or substituted with at least one halogen, $R_3$ is selected from the group consisting of hydrogen, alkyl of 1 to 3 carbon atoms, —CN and C=CH and A is selected from the group consisting of

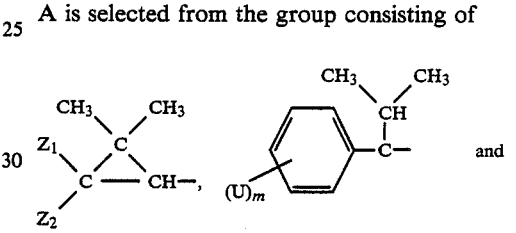

wherein $Z_1$ and $Z_2$ are methyl or $Z_1$ is hydrogen and $Z_2$ is selected from the group consisting of

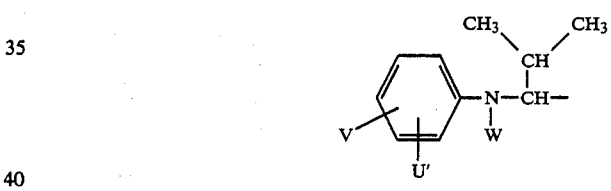

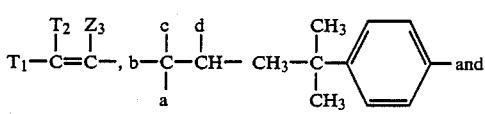

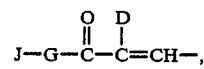

$Z_3$ is hydrogen or halogen, $T_1$ and $T_2$ are individually selected from the group consisting of hydrogen, halogen, —$CF_3$, —CN, phenyl unsubstituted or substituted with a halogen and alkyl and alkoxy of 1 to 8 carbon atoms, B is —O— or —S—, a,b,c, and d are individually halogen, D is selected from the group consisting of hydrogen, halogen and alkoxy of 1 to 8 carbon atoms, G is —O— or —S— J is alkyl of 1 to 8 carbon atoms unsubstituted or substituted with at least one halogen, aryl of 6 to 14 carbon atoms, the latter unsubstituted or substituted with at least one functional group, U is selected from the group consisting of halogen and alkyl and alkoxy of 1 to 8 carbon atoms unsubstituted or substituted with at least one halogen, m is 0, 1 or 2 and if 2, the Us may be different, U' and V are individually selected from the group consisting of hydrogen, halogen, and —CF₃ and W is hydrogen or —CH₃.

2. A compound of claim 1 wherein R₃ is hydrogen.
3. A compound of claim 1 wherein R₁ is alkenyl or alkynyl of 2 to 4 carbon atoms.
4. A compound of claim 1 wherein R₁ is 2-propynyl.
5. A compound of claim 1 wherein R₁ is 2-propenyl.
6. A compound of claim 1 wherein R₂ is —CF₃.
7. A compound of claim 1 wherein A is

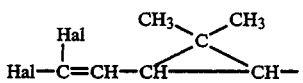

and Hal ia fluorine, chlorine, bromine or iodine.

8. A compound of claim 7 wherein Hal is bromine.
9. A compound of claim 1 wherein A is

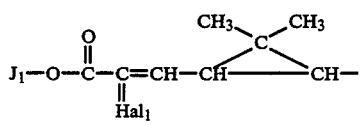

wherein Hal₁ is a halogen, J₁ is selected from the group consisting of alkyl of 1 to 8 carbon atoms and cycloalkyl of 3 to 8 carbon atoms, both optionally substituted with one or more halogens and the double bond has E geometry.

10. A compound of claim 9 wherein Hal₁ is fluorine.
11. A compound of claim 1 wherein A is

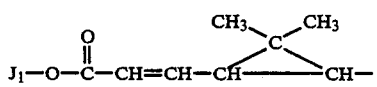

wherein J₁ is selected from the group consisting of alkyl of 1 to 8 carbon atoms and cycloalkyl of 3 to 8 carbon atoms, both optionally substituted with one or more halogens and the double bond has Z geometry.

12. A compound of claim 11 wherein J₁ is tert.-butyl.
13. A compound of claim 11 wherein J₁ is

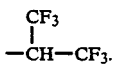

14. A compound of claim 1 wherein A is

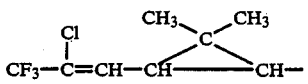

15. A compound of claim 1 selected from the group consisting of [2-oxo-3-(2-propynyl)-4-trifluoromethyl-2,3-dihydrothiazol-5-yl]-methyl [1R [1α, 3α, ΔZ]] 2,2-dimethyl-3-[2-chloro-3,3,3-trifluoropropenyl]-cyclopropane carboxylate; [2-oxo-3-(2-propynyl)-4-trifluoromethyl-2,3-dihydrothiazol-5-yl]-methyl [1R [1α, 3α, ΔZ]] 2,2-dimethyl-3-[3-oxo-3-(1,1,1,3,3,3-hexafluoro-2-propyloxy)-1-propenyl]-cyclopropane carboxylate; [2-oxo-3-(2-propynyl)-4-trifluoromethyl-2,3-dihydrooxazol-5-yl]-methyl [1R [1α, 3α, ΔE]] 2,2-dimethyl-3-[3-oxo-3-(1,1-dimethyl-ethoxy)-2-fluoropropenyl]-cyclopropane carboxylate; [2-oxo-3-(2-propynyl)-2,3-dihydrothiazol-5-yl]-methyl [1R [1α, 3α, ΔE]] 2,2-dimethyl-3-[2-fluoro-3-oxo-3-(2,2-dimethylethoxy)-1-propenyl]-cyclopropane carboxylate; and [2-oxo-3-(2-propynyl)-4-methyl-2,3-dihydrothiazol-5-yl]-methyl [1R [1α, 3α, ΔE]] 2,2-dimethyl-3-(2-fluoro-3-oxo-3-ethoxy-propenyl)-cyclopropane carboxylate.

16. An insecticidal composition comprising an insecticidally effective amount of at least one compound of claim 1 and an inert carrier.
17. A composition of claim 16 wherein R₃ is hydrogen.
18. A composition of claim 16 wherein R₁ is alkenyl or alkynyl of 2 to 4 carbon atoms.
19. A composition of claim 16 wherein R₁ is 2-propynyl.
20. A composition of claim 16 wherein R₁ is 2-propenyl.
21. A composition of claim 16 wherein R₂ is —CF₃.
22. A composition of claim 16 wherein A is

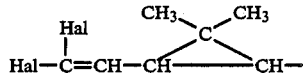

and Hal is fluorine, chlorine, bromine or iodine.

23. A composition of claim 16 wherein Hal is bromine.
24. A composition of claim 16 wherein A is

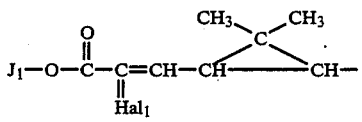

wherein Hal₁ is a halogen, J₁ is selected from the group consisting of alkyl of 1 to 8 carbon atoms and cycloalkyl of 3 to 8 carbon atoms, both optionally substituted with one or more halogens and the double bond has E geometry.

25. A composition of claim 16 wherein Hal₁ is fluorine.
26. A composition of claim 16 wherein A is

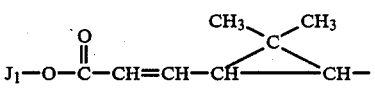

wherein J₁ is selected from the group consisting of alkyl of 1 to 8 carbon atoms and cycloalkyl of 3 to 8 carbon atoms, both optionally substituted with one or more halogens and the double bond has Z geometry.

27. A composition of claim 16 wherein J₁ is tert-butyl.
28. A composition of claim 16 wherein J₁ is

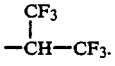

29. A composition of claim 16 wherein A is

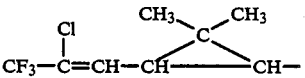

30. A composition of claim 16 wherein the active compound is selected from the group consisting of [2-oxo-3-(2-propynyl)-4-trifluoromethyl-2,3-dihydrothiazol-5-yl]methyl [1R [1α, 3α, ΔZ]] 2,2-dimethyl-3-[2-chloro-3,3,3-trifluoropropenyl]-cyclopropane carboxylate; [2-oxo-3-(2-propynyl)-4-trifluoromethyl-2,3-dihydrothiazol-5-yl]-methyl [1R [1α, 3α, ΔZ]] 2,2-dimethyl-3-[3-oxo-3-(1,1,1,3,3,3-hexafluoro-2-propyloxy)-1-propenyl]-cyclopropane carboxylate; [2-oxo-3-(2-propynyl)-4-trifluoromethyl-2,3-dihydrooxazol-5-yl]-methyl [1R [1α, 3α, ΔE]] 2,2-dimethyl-3-[3-oxo-3-(1,1-dimethylethoxy)-2-fluoropropenyl]-cyclopropane carboxylate; [2-oxo-3-(2-propynyl)-2,3-dihydrothiazol-5-yl]-methyl [1R [1α, 3α, ΔE]] 2,2-dimethyl-3-[2-fluoro-3-oxo-3-(2,2-dimethylethoxy)-1-propenyl]-cyclopropane carboxylate; and [2-oxo-3-(2-propynyl)-4-methyl-2,3-dihydrothiazol-5-yl]-methyl [1R [1α, 3α, ΔE]] 2,2-dimethyl-3-(2-fluoro-3-oxo-3-ethoxy-propenyl)-cyclopropane carboxylate.

31. An acaricidal composition comprising an acaricidally effective amount of at least one compound of claim 1 and an inert carrier.

32. A nematocidal composition comprising a nematocidally effective amount of at least one compound of claim 1 and an inert carrier.

33. A composition of claim 16 also containing at least one of the pyrethrinoid esters selected from the group consisting by esters of allethrolone, of 3,4,5,6-tetrahydrophthalimido-methyl alcohol, of 5-benzyl-3-furyl-methyl alcohol, of 3-phenoxy-benzyl alcohol and of α-cyano-3-phenoxy-benzyl alcohols with chrysanthemic acids, by the esters of 5-benzyl-3-furyl-methyl alcohol with 2,2-dimethyl-3-(2-oxo-3,4,5,6-tetra-hydrothiophenylidene methyl)-cyclopropane-1-carboxylic acids, by the esters of 3-phenoxy-benzyl alcohol and of α-cyano-3-phenoxy-benzyl alcohols with 2,2-dimethyl-3-(2,2-dichlorovinyl)-cyclopropane-1-carboxylic acids, by esters of α-cyano-3-phenoxy-benzyl alcohol with 2,2-dimethyl-3-(2,2-dibromovinyl)-cyclopropane-1-carboxylic acids, by the esters of 3-phenoxy-benzyl alcohol with 2-parachlorophenyl-2-isopropyl acetic acids, by esters of allethrolones, of 3,4,5,6-tetrahydrophthalimido-methyl alcohol, of 5-benzyl-3-furylmethyl alcohol, of 3-phenoxy-benzyl alcohol and of α-cyano-3-phenoxy-benzyl alcohols with the 2,2-dimethyl-3-(1,2,2,2-tetrahaloethyl)-cyclopropane-1-carboxylic acids, in which "halo" represents a fluorine, chlorine or bromine atom, in all their possible stereoisomeric forms of the pyrethrinoid esters.

34. A composition of claim 16 also containing a pyrethrinoid synergist.

35. A method of combatting insecticides comprising contacting the insects with an insecticidally effective amount of at least one compound of claim 1.

36. A method of claim 35 wherein $R_3$ is hydrogen.

37. A method of claim 35 wherein $R_1$ is alkenyl or alkynyl of 2 to 4 carbon atoms.

38. A method of claim 35 wherein $R_1$ is 2-propynyl.

39. A method of claim 35 wherein $R_1$ is 2-propenyl.

40. A method of claim 35 wherein $R_2$ is —CF$_3$.

41. A method of claim 35 wherein A is

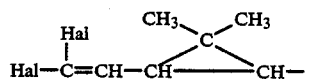

and Hal is fluorine, chlorine, bromine or iodine.

42. A method of claim 35 wherein Hal is bromine.

43. A method of claim 35 wherein A is

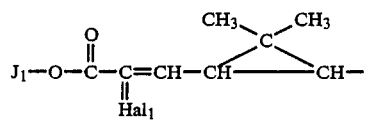

wherein Hal$_1$ is a halogen, J$_1$ is selected from the group consisting of alkyl of 1 to 8 carbon atoms and cycloalkyl of 3 to 8 carbon atoms, both optionally substituted with one or more halogens and the double bond has E geometry.

44. A method of claim 35 wherein Hal$_1$ is fluorine.

45. A method of claim 35 wherein A is

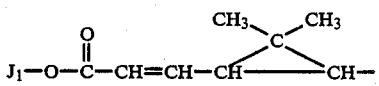

wherein J$_1$ is selected from the group consisting of alkyl of 1 to 8 carbon atoms and cycloalkyl of 3 to 8 carbon atoms, both optionally substituted with one or more halogens and the double bond has Z geometry.

46. A method of claim 35 wherein J$_1$ is tert-butyl.

47. A method of claim 35 wherein J$_1$ is

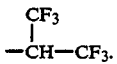

48. A method of claim 35 wherein A is

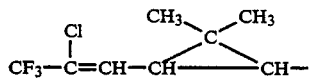

49. A method of claim 35 selected from the group consisting of [2-oxo-3-(2-propynyl)-4-trifluoromethyl-2,3-dihydrothiazol-5-yl]-methyl [1R [1α, 3α, ΔZ]] 2,2-dimethyl-3-[2-chloro-3,3,3-trifluoropropenyl]-cyclopropane carboxylate; [2-oxo-3-(2-propynyl)-4-trifluromethyl-2,3-dihydrothiazol-5-yl]-methyl [1R [1α, 3α, ΔZ]] 2,2-dimethyl-3-[3-oxo-3-(1,1,1,3,3,3-hexafluoro-2-propyloxy)-1-propenyl]-cyclopropane-carboxylate; [2-oxo-3-(2-propynyl)-4-trifuoromethyl-2,3-dihydrooxazol-5-yl]-methyl [1R [1α, 3α, ΔE]] 2,2-dimethyl-3-[3-oxo-3-(1,1-dimethyl-ethoxy)-2-fluoro-propenyl]-cyclopropane carboxylate; [2-oxo-3-(2-propynyl)-2,3-dihydrothiazol-5-yl]-methyl [1R [1α, 3α, ΔE]] 2,2-dimethyl-3-[2-fluoro-3-oxo-3-(2,2-dimethylethoxy)-1-propenyl]-cyclopropane carboxylate; and [2-oxo-3-(2-propynyl)-4-methyl-2,3-dihydrothiazol-5-yl]-methyl [1R [1α, 3α, ΔE]] 2,2-dimethyl-3-(2-fluoro-3-oxo-3-ethoxy-propenyl)-cyclopropane carboxylate.

50. A method of combatting acariens comprising contacting acarien with an acaridically effective amount of at least one compound of claim 1.

51. A method of combatting nematodes comprising contacting nematodes with a nematocidally effective amount of at least one compound of claim 1.

* * * * *